US008765373B2

(12) United States Patent
Majda

(10) Patent No.: US 8,765,373 B2
(45) Date of Patent: Jul. 1, 2014

(54) SENSOR AND METHOD FOR DETECTION OF A TARGET SUBSTANCE

(75) Inventor: Marcin Majda, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 312 days.

(21) Appl. No.: 13/113,467

(22) Filed: May 23, 2011

(65) Prior Publication Data

US 2013/0172202 A1 Jul. 4, 2013

Related U.S. Application Data

(60) Division of application No. 11/238,635, filed on Sep. 28, 2005, now abandoned, which is a continuation-in-part of application No. 11/080,064, filed on Mar. 14, 2005, now abandoned, which is a continuation-in-part of application No. 10/944,140, filed on Sep. 16, 2004, now abandoned.

(60) Provisional application No. 60/504,334, filed on Sep. 17, 2003.

(51) Int. Cl.
*C12Q 1/68* (2006.01)
*G01N 33/53* (2006.01)
*C12M 1/00* (2006.01)
*C12M 1/34* (2006.01)
*C40B 30/04* (2006.01)
*C07H 21/02* (2006.01)

(52) U.S. Cl.
USPC ....... 435/6.1; 435/7.1; 435/283.1; 435/287.2; 506/9; 536/23.1

(58) Field of Classification Search
USPC .................. 435/6.1, 7.1, 283.1, 287.2; 506/9; 536/23.1
See application file for complete search history.

(56) References Cited

U.S. PATENT DOCUMENTS

| 5,300,423 | A | 4/1994 | Zoha et al. |
| 5,861,244 | A | 1/1999 | Wang et al. |
| 6,093,536 | A | 7/2000 | Drake et al. |
| 6,180,418 | B1 | 1/2001 | Lee |
| 2002/0048760 | A1 | 4/2002 | Drmanac et al. |
| 2003/0035810 | A1 | 2/2003 | Caplan |
| 2003/0054376 | A1* | 3/2003 | Mullis et al. ...................... 435/6 |
| 2003/0215825 | A1 | 11/2003 | Tong |

FOREIGN PATENT DOCUMENTS

WO      WO 02/42498      5/2002

OTHER PUBLICATIONS

Clark, L. C., Electrode Systems for Continuous Monitoring in Cardiovascular Surgery, *Ann. N. Y. Acad. Sci.* 1962, 102, 29-45.
Lauks, I. R., Microfabricated Biosensors and Microanalytical Systems for Blood Analysis, *Acc. Chem. Res.*, 1998, 31, 317-324.
Landers, J. P. Molecular Diagnostics on Electrophoretic Microchips, *Anal. Chem.* 2003, 75, 2919-2927.
Figeys, D.; Pinto, D., Lab-on-a-Chip: A Revolution on Biological and Medical Sciences, *Anal Chem.* 2000, 72, 330A-335A.
Palcek, E.; Fojta, M., DNA Hybridization and Damage, *Anal Chem.* 2001, 73, 75A-83A.
Invnitski, D.; Abdel-Hamid. I.; Atanasov, P.; Wilkins, E., Biosensors for the Detection of Pathogenic Bacteria, *Biosens. Bioelectron.* 1999, 14, 599-624.
Charych, D. H.; Nagy, J. O.; Spevak, W.; Bednarski, M. D., Direct Colorimetric Detection of a Receptor-Ligand Interaction by a Polymerized Bilayer Assembly, *Science*, 1993, 261, 585-588.
Baeck, M.-G,; Stevens, R. C.; Charych, D. H., Design and Synthesis of Novel Glycopolythiophene Assemblies for Colorimetric Detection of Influenza Virus and *E. Coli, Bioconjugate Chem.* 2000, 11, 777-788.
Xu, X.-H.; Bard, A. J., Immobilization and Hybridization of DNA on an Aluminum(III) Alkanebisphosphonate Thin Film with Electrogenerated Chemiluminescent Detection, *J. Am. Chem. Soc.* 1995, 117, 2627-2631.
Livache, T.; Fouque, B.; Roget, A.; Marchand, R.; Bidan, G.; Téoule, R.; Mathis, G., Polypyrrole DNA Chip on a Silicon Device: Example of Hepatitis C Virus Genotyping, *Anal. Biochem.* 1998, 255, 188-194.
Bonnet, G.; Tyagi, S.; Libchaber, A.; Kramer, F. R., Thermodynamic Basis of the Enhanced Specificity of Structured DNA Probes, *Proc. Natl. Acad. Sci. USA* 1999; 96, 6171-6176.
Heaton, R.J.; Peterson, A.W.; Georgiadis, R.M., Electrostatic Surface Plasmon Resonance: Direct Electric Field-Induced Hybridization and Denaturation in Monolayer Nucleic Acid Films and Label-Free Discrimination of Base Mismatches, *Proc. Natl. Acad. Sci. USA* 2001, 98, 3701-3704.
Peterson, A. W.; Heaton, R. J.; Georgiadis, R. M., The Effect of Surface Probe Density on DNA Hybridization, *Nucleic Acids Research*, 2001, 29, 5163-5168.
Peterson, A. W.; Wolf, L. K.; Georgiadis, R. M., Hybridization of Mismatched or Partially Matched DNA at Surfaces, *J. Am. Chem. Soc.* 2002, 124, 14601-14607.
Wei, Y.; Cao, C.; Jin, R.; Mirkin, C. A., Nanoparticles with Raman Spectroscopic Fingerprints for DNA and RNA Detection, *Science* 2002, 297, 1536-1540.
Gaylord, B. S.; Heeger, A. J.; Bazan, G. C. DNA Detection Using Water-Soluble Conjugated Polymers and Peptide Nucleic Acid Probes, *Proc. Natl. Acad. Sci. USA* 2002, 99, 10954-10957.
Liebermann, T.; Knoll, W., Parallel Multispot Detection of Target Hybridization to Surface-Bound Probe Oligonucleotides of Different Base Mismatch by Surface-Plasmon Field-Enhanced Fluorescence Microscopy, *Langmuir* 2003, 19, 1567-1572.

(Continued)

*Primary Examiner* — Narayan Bhat
(74) *Attorney, Agent, or Firm* — Weaver Austin Villeneuve & Sampson LLP

(57) ABSTRACT

A method of detecting a target substance includes providing a number of molecular tethers at a channel surface of a sensor such that at least some of a plurality of beads, as a result of a biological interaction between a target substance and the tethers, are attached to the channel surface by the tethers or released from the channel's surface by cleaving the tethers. This method further includes introducing an analyte into the channel and determining the population of beads at the channel surface to indicate a presence of the target substance in the analyte.

11 Claims, 5 Drawing Sheets

(56) References Cited

OTHER PUBLICATIONS

Piestert, O.; Barsch, H.; Buschmann, V.; Heinlein, T.; Knemeyer, J.-P.; Weston, K. D.; Sauer, M., A Single Molecule Sensitive DNA Hairpin System Based n Intramolecular Electron Transfer, *Nano Lett.* 2003, 3, 979-982.

Bailey, R. C.; Nam, J.-M.; Mirkin, C. A.; Hupp, J. T., Real-Time Multicolor DNA Detection with Chemoresponsive Diffraction Gratings and Nanoparticle Probes, *J. Am. Chem. Soc.* 2003, 125, 13541-13547.

Fritz, J.; Cooper, E. B.; Gaudet, S.; Sorger, P. K.; Manalis, S. R., Electronic Detection of DNA by its Intrinsic Molecular Charge, *Proc. Natl. Acad. Sci. USA* 2002, 99, 14142-14146.

Park, S. J.; Taton, T. A.; Mirkin, C. A., Array-Based Electrical Detection of DNA with Nanoparticle Probes, *Science* 2002, 295, 5559, 1503-1506.

Singhal, P.; Kuhr, W. G., Ultrasensitive Voltammetric Detection of Underivatized Oligonucleotides and DNA, *Anal. Chem.* 1997, 69, 4828-4832.

Steel, A. B.; Herne, T. M.; Tarlov, M. J., Electrochemical Quantitation of DNA Immobilized on Gold, *Anal. Chem.* 1998; 70, 4670-4677.

Wang, J.; Bollo, S.; Lopez Paz, J. L.; Sahlin, E.; Mukherjee, B., Ultratrace Measurements of Nucleic Acids by Baseline-Corrected Adsorptive Stripping Square-Wave Voltammetry, *Anal. Chem.* 1999; 71, 1910-1913.

Armistead, P. M.; Thorp, H. H., Modification of Indium Tin Oxide Electrodes with Nucleic Acids: Detection of Attomole Quantities of Immobilized DNA by Electrocatalysis, *Anal. Chem.* 2000; 72, 3764-3770.

Kelley, S.O.; Boon, E. M.; Barton, J. K.; Jackson, N. M.; Hill, M. G., Single-Base Mismatch Detection Based on Charge Transduction through DNA, *Nucleic Acids Res.* 1999, 27, 4830-4837.

Boon, E. M.; Ceres, D. M.; Drummond, T. G.; Hill, M. G.; Barton, J. K., Mutation Detection by Electrocatalysis at DNA-Modified Electrodes, *Nat. Biotechnol.* 2000, 18, 1096-1100.

Patolsky, F.; Lichtenstein, A.; Willner, I., Electronic Transduction of DNA Sensing Processes on Surfaces: Amplification of DNA Detection and Analysis of Single-Base Mismatches by Tagged Liposomes, *J. Am. Chem. Soc.* 2001, 123, 5194-5205.

Patolsky, F.; Weizmann, Y.; Willner, I., Redox-Active Nucleic-Acid Replica for the Amplified Bioelectrocatalytic Detection of Viral DNA, *J. Am. Chem. Soc.* 2002, 124, 770-772.

Fan, CX.; Plaxco, K. W.; Heeger, A. J., Electrochemical Interrogation of Conformational Changes as a Reagentless Method for the Sequence-Specific Detection of DNA, *Proc. Natl. Acad. Sci. USA* 2003, 100, 9134-9137.

Cheng, Q.; Peng, T.; Stevens, R. C., Signaling of *Escherichia Coli* Enterotoxin on Supramolecular Redox Bilayer Vesicles, *J. Am. Chem. Soc.* 1999, 121, 6767-6768.

J. Janin et al., "The structure of protein-protein recognition sites", *J. Biol. Chem.*, 1990, 265, 16027-16030.

N. Jentoff et al., "Labeling of proteins by reductive methylation using sodium cyanoborohydride", *J. Biol. Chem.*, 1979, 254, 4359-4365.

R. H. Rice et al., "Stabilization of bovine trypsin by reductive methylation", *Biochim. Biophys. Acta*, 1977, 492, 316-321.

R.L. Lundblad, "Chemical Reagents for Protein Modification", 3$^{rd}$ Edition., *CRC Press*, Boca Raton, Fl. 2005 pp. 48-51

M.J.P. Dekker et al., Identification of a second active site residue in *Escherichia coli* I-threonine dehydrogenase: methylation of histidine-90 with methyl p-nitrobenzenesulfonate, *Arch. Biochem. Biophys*, 1995, 316, 413-420.

J.F. Schindler et al., "Conversion of cysteinyl residues to unnatural amino acid analogues", *J. Protein Chem.*, 1996, 15, 737-742.

R.L. Lundblad, "Chemical Reagents for Protein Modification", 3$^{rd}$ Edition., *CRC Press*, Boca. Raton, Fl. 2005 pp. 213-215

H.M. Levy et al, "Inactivation of myosin by 2,4-dinitrophenol and protection by adenosine triphosphate and other phosphate compounds", *J. Biol. Chem.*, 1963, 238, 3654-3659.

K. Takahashi, "The reaction of phenylglyoxal with arginine residues in proteins", *J. Biol. Chem.*, 1968, 243, 6171-6179.

R.B. Woodward et al, "A new synthesis of peptides", *J. Am. Chem. Soc.*, 1961, 83, 1010-1012.

P. Bodlaender et al, "The use of isoxazolium salt for carboxyl group modification in proteins", *Biochemistry*, 1969, 8, 4941.

de Jong, M. O.; Rozemuller, H.; Bauman, J. G. J.; Visser, J. W. M., "Biotinylation of interleukin-2 (IL-2) for flow cytometric analysis of IL-2 receptor expression", *J. Immun. Meth*, 1995, 184, 101-112.

Kulin, Simone; Kishore, Rani; Hubbard, Joseph; Helmerson, Kristian. Real-time measurement of spontaneous antigen-antibody dissociation. Biophys. J., 2002, 83, 1965-1973.

U.S. Appl. No. 60/504,334, filed Sep. 17, 2003 (expired).
U.S. Appl. No. 10/944,140, filed Sep. 16, 2004 (abandoned).
U.S. Appl. No. 11/080,064, filed Mar. 14, 2005 (abandoned).
U.S. Appl. No. 11/238,635, filed Sep. 28, 2005 (published).
Office Action in U.S. Appl. No. 11/238,635 dated Jul. 23, 2007.
Final Office Action in U.S. Appl. No. 11/238,635 dated Jun. 4, 2008.
Office Action in U.S. Appl. No. 11/238,635 dated Feb. 10, 2009.
Final Office Action in U.S. Appl. No. 11/238,635 dated Sep. 28, 2009.
Office Action in U.S. Appl. No. 11/238,635 dated May 14, 2010.
Final Office Action in U.S. Appl. No. 11/238,635 dated Nov. 22, 2010.

* cited by examiner

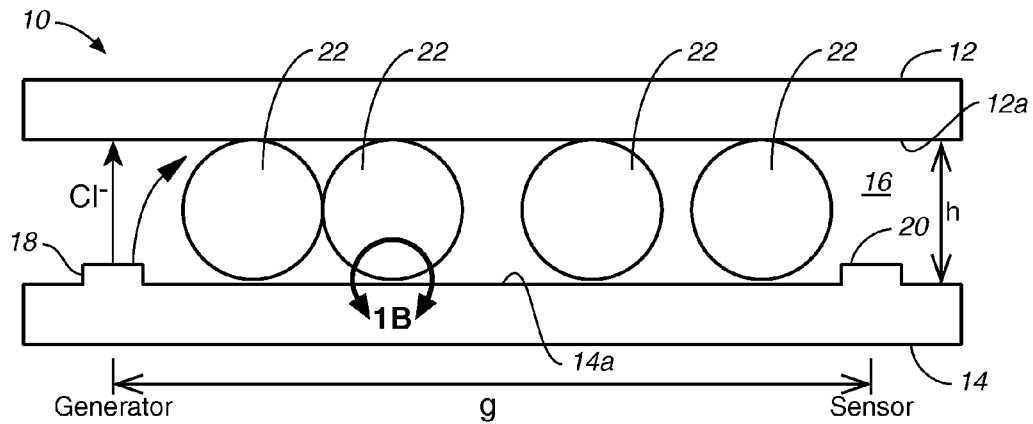
FIG._1A
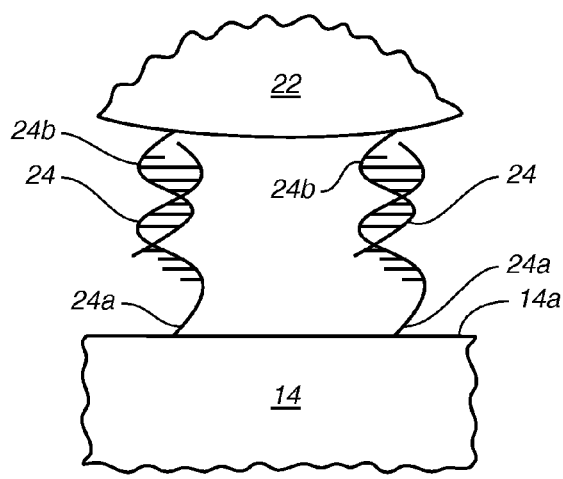
FIG._1B
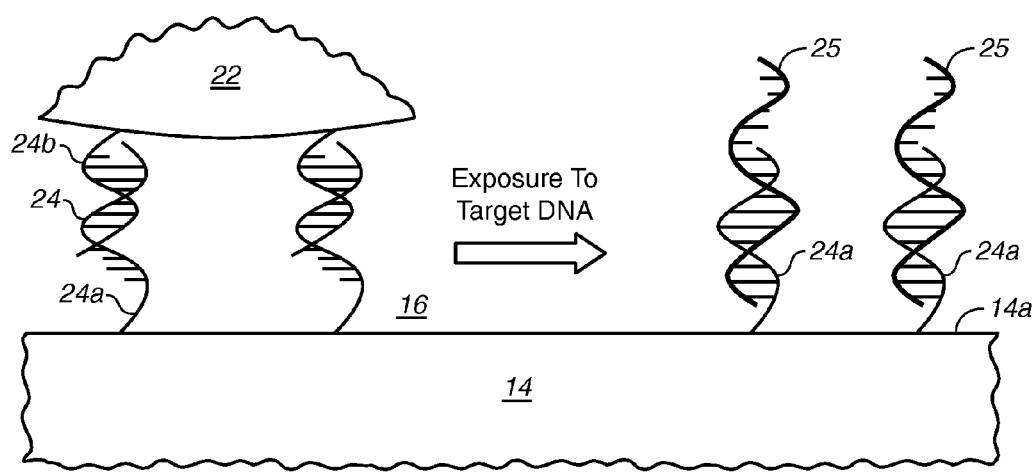
FIG._1C

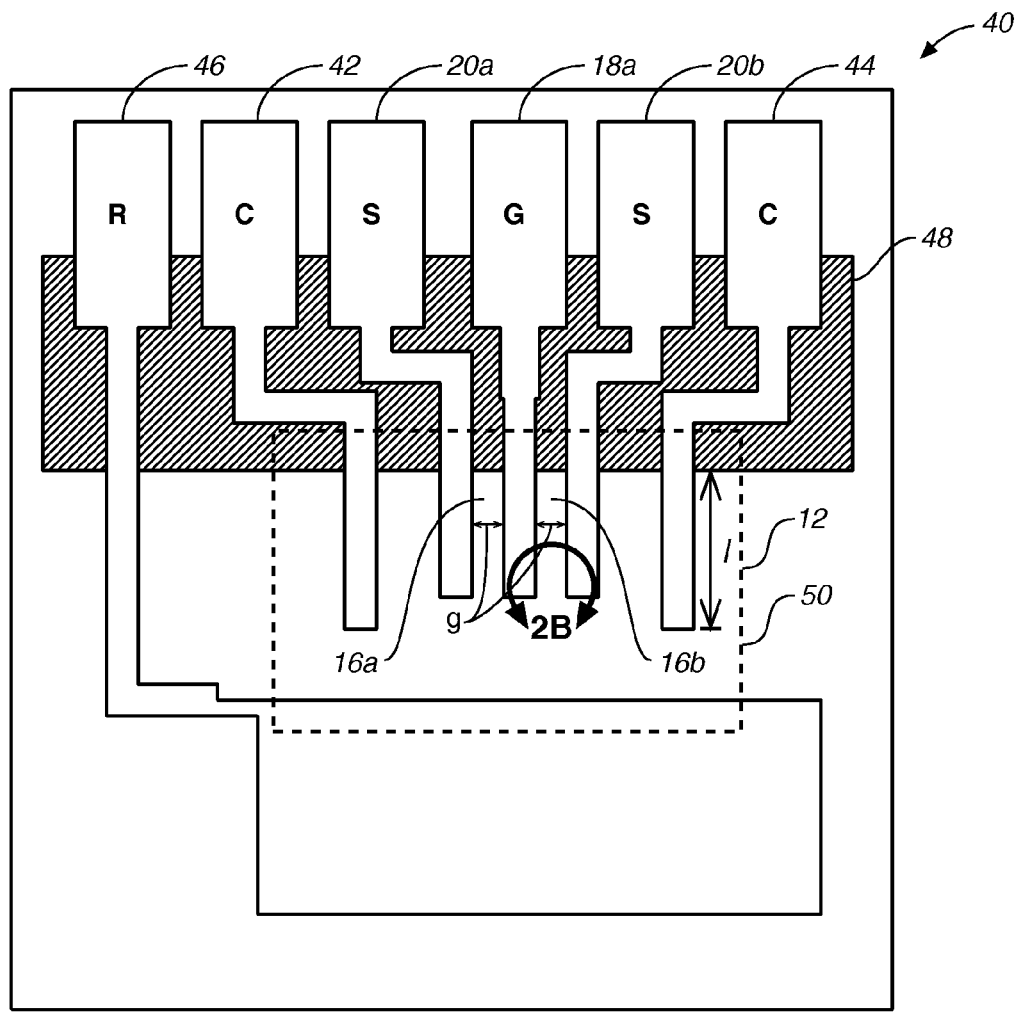
FIG._2A
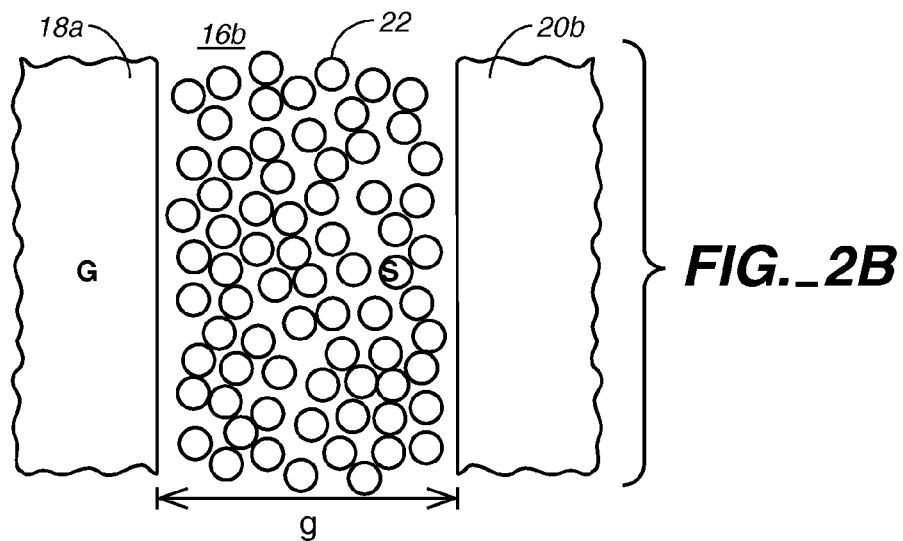
FIG._2B

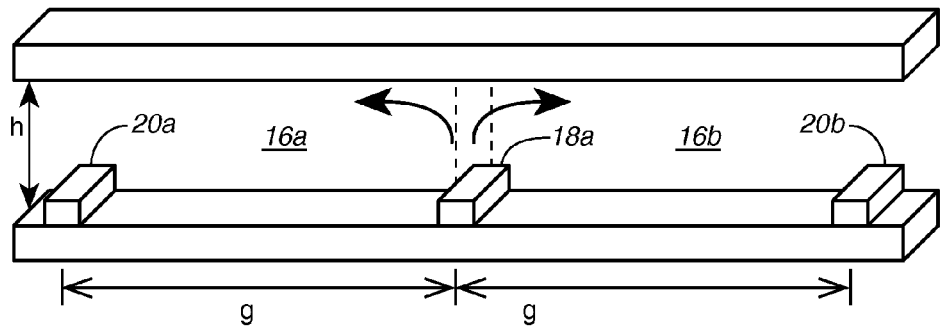
FIG._2C
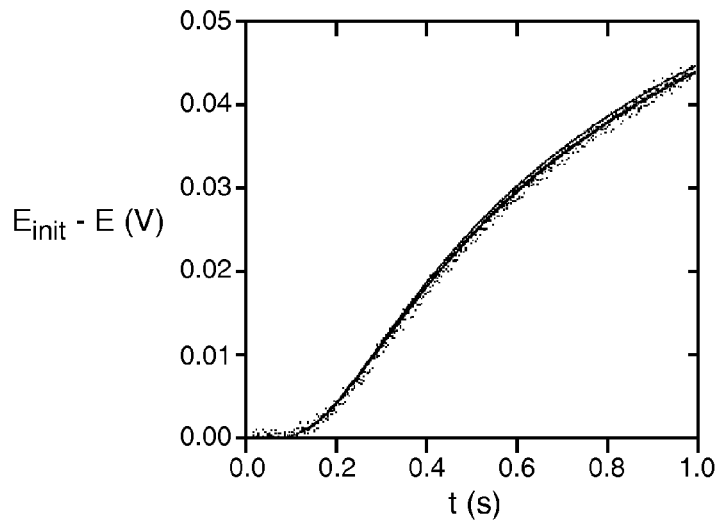
FIG._3
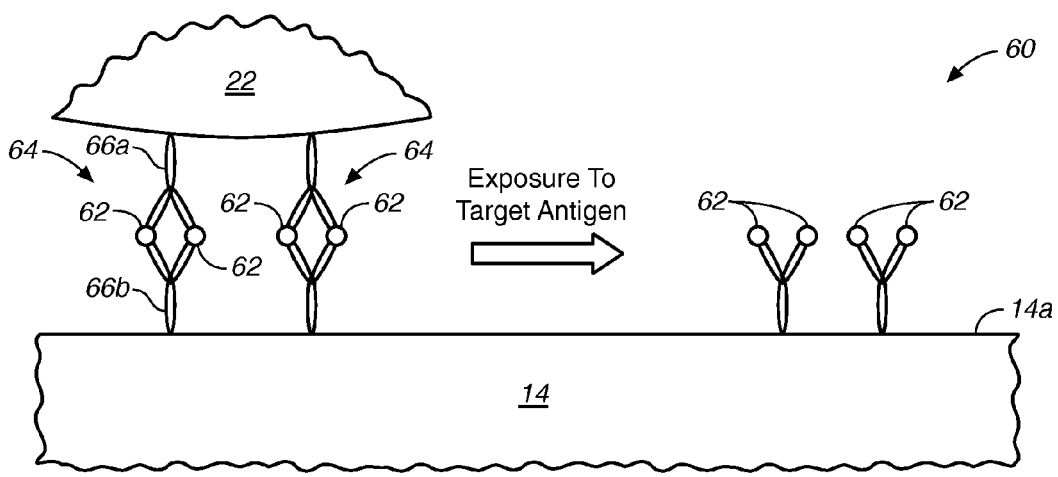
FIG._4

SENSOR AND METHOD FOR DETECTION OF A TARGET SUBSTANCE

CROSS REFERENCE TO RELATED APPLICATIONS

This application is a divisional of U.S. patent application Ser. No. 11/238,635, filed on Sep. 28, 2005 now abandoned entitled "A Sensor And Method For Detection Of A Target Substance", which is a continuation-in-part of U.S. patent application Ser. No. 11/080,064, filed Mar. 14, 2005, now abandoned entitled "A Sensor And Method For Detection Of A Target Substance", which is a continuation-in-part of U.S. patent application Ser. No. 10/944,140, filed Sep. 16, 2004, now abandoned entitled "A Sensor And Method For Detection Of A Target Substance", which claims priority under 35 U.S.C. 119(e) from Provisional U.S. Patent Application Ser. No. 60/504,334, filed Sep. 17, 2003, entitled "Electrochemical, Reagentless, Hand-Held Sensor And Method For Detection Of DNA Hybridization And Other Molecular Binding And Cleaving Events", both of which are incorporated herein by reference.

STATEMENT REGARDING FEDERALLY SPONSORED RESEARCH

The techniques and mechanisms of the present invention were made with Government support under National Science Foundation Grant No. CHE0079225.

BACKGROUND

The modern concept of biological sensors evolved considerably over the forty years since it was first demonstrated that enzymes could be immobilized at a surface of an electrochemical detector. Demands to reduce the sample volume, the cost and the time of analysis, and to increase sensitivity and selectivity have been most pressing in biological and biomedical sciences. This has fueled development of microanalytical devices and bio-sensors with a wide range of applications in the clinical and defense settings, in gene and forensic analysis, in environmental monitoring, food safety and many other settings. While selectivity of biological sensors always derives from the unique molecular recognition interactions, such as antibody-antigen binding or complimentary deoxyribonucleic acid (DNA) hybridization, transduction and amplification of these events into analytically useful signal is often a major challenge.

Interest in detecting DNA in a sequence-specific manner has grown steadily in recent years. The ability to rapidly and inexpensively detect DNA of specific sequences may allow more efficient pathogen, point mutation and gene detection. Multiple approaches of detecting DNA in a sequence-specific fashion have been explored, including optical (for example, chemiluminescence fluorescence, Raman spectroscopic and surface plasmon resonance), electronic as well as numerous electrochemical methods. Historically, fluorescence methods have been the most sensitive. However, advances in the electrochemical detection of DNA are becoming competitive in terms of sensitivity.

Detection of pathogenic species in water is also an important and challenging problem. Several examples reporting direct response sensor devices sensitive to bacteria, viruses and bacterial toxins exist. These include, for example, colorimetric sensors designed to detect influenza virus and *E. Coli* and an electrochemical sensor responding to *E. Coli* enterotoxin.

These technologies, however, have certain disadvantages. It is therefore desirable to provide improved methods and apparatus for electrochemical sensing of a target substance. In one example, it is desirable to provide sensors having microfabrication efficiencies that are highly accurate and yet inexpensive enough so that they are disposable.

SUMMARY

In one aspect, the invention features a sensor. The sensor comprises molecular tethers attached to a sensor surface such that at least some of a plurality of beads, as a result of a biological interaction between a target substance and the tethers, can at least one of be attached to the sensor surface by the tethers or released from the sensor surface by cleaving the tethers. The sensor further includes a measurement system configured and arranged to determine the population of beads at the sensor surface after the introduction of the analyte into the sensor.

Various implementations of the invention may include one or more of the following features. A tether includes a hybrid double-stranded DNA molecule, an antibody, a modified antibody, a modified antigen or a peptide.

In yet another aspect, the invention is directed to a sensor to determine if a target substance is present in an analyte. The sensor comprises a plurality of beads located in a channel and attached to a surface of the channel by a molecular tether. The tether can be selectively cleaved in the presence of a target substance to release at least some of the beads from the surface of the channel. The sensor further includes a measurement system configured and arranged to determine the population of beads in the channel after the introduction of the analyte into the channel.

Various implementations of the invention may include one or more of the following features. The target substance is a target antigen and a molecular tether includes a modified antigen and an antibody with the modified antigen having a lower binding constant than the target antigen. The modified antigen has an approximately 2 orders of magnitude lower binding constant than the target antigen. The target substance is a target DNA and a molecular tether is a hybridized double-stranded DNA tether with one of the single-stranded DNA fragments of the double-stranded DNA tether being complementary to the target DNA. The hybridized double-stranded DNA tether includes first and second single-strand DNA fragments. The first single-strand DNA fragment is attached to a surface of the channel, and the sequence of the first single-strand DNA fragment is complementary to the target DNA. The second single-strand DNA fragment is attached to a surface of a bead. The measurement system may be a signal transduction system, a conductivity measurement system, a coulometric measurement system, a spectrometric measurement system, an optical measurement system, or an electrochemical counting system.

In another aspect, the invention is directed to a sensor to detect a target antigen. The sensor comprises a plurality of beads attached to a sensor surface by a modified antigen and an antibody wherein the modified antigen has a lower binding constant than the target antigen.

In still another aspect, the invention is directed to a sensor to detect a target antibody. The sensor comprises a plurality of beads attached to a sensor surface by a modified antibody and an antigen wherein the modified antibody has a lower binding constant than the target antibody.

In another aspect, the invention is directed to a sensor to detect a target substance in an analyte. The sensor comprises a channel and a plurality of beads are located in the channel and attached to a surface of the channel by a molecular tether. The tether can be selectively cleaved in the presence of a target substance to release at least some of the beads from the surface of the channel. Measurement means are provided for determining the population of beads in the channel after the introduction of the analyte into the channel.

In yet another aspect, the invention features a method of detecting a target substance. The method includes providing a number of molecular tethers at a channel surface of a sensor such that at least some of a plurality of beads, as a result of a biological interaction between a target substance and the tethers, can at least one of be attached to the channel surface by the tethers or released from the channel surface by cleaving the tethers. An analyte is introduced into the channel. Thereafter, the population of beads at the channel surface is determined to indicate a presence of the target substance in the analyte.

Various implementations of the invention may include one or more of the following features. The tethers include a hybrid double-stranded DNA molecule, an antibody, a modified antibody, a modified antigen or a peptide. The target substance is a target DNA and a molecular tether is a hybridized double-stranded DNA tether with one of the single-stranded DNA fragments of the double-stranded tether being complementary to the target DNA. The hybridized double-stranded DNA tether includes first and second single-strand DNA fragments. The first single-strand DNA fragment is attached to a surface of the channel, and the sequence of the first single-strand DNA fragment is complementary to the target DNA. The second single-strand DNA fragment is attached to a surface of a bead.

Other implementations of the invention may include one or more of the following features. The target substance is a target antigen and a molecular tether includes a modified antigen and an antibody with the modified antigen having a lower binding constant than the target antigen. The target substance is a target antibody and a molecular tether includes a modified antibody and an antigen with the modified antibody having a lower binding constant than the target antibody.

The invention can include one or more of the following advantages. The sensor can detect a target substance such as DNA and a range of immunogens (antigens), a large group of macromolecules including cancer-specific proteins, toxins and numerous other pathogens. The sensor may be microfabricated and made small enough to be hand-held. The sensor may be disposable. The sensor functions without the use of reagents. The sensor may be part of an array. Each sensor of the array may respond to a specific DNA sequence. The sensor can simultaneously detect different target substances in sub-micron liter (uL) volumes of a solution at nano-Molar (nM) concentration levels.

These and other features and advantages of the present invention will be presented in more detail in the following specification of the invention and the accompanying figures, which illustrate, by way of example, the principles of the invention.

BRIEF DESCRIPTION OF DRAWINGS

The invention may best be understood by reference to the following description taken in conjunction with the accompanying drawings that illustrate specific embodiments of the present invention.

FIG. 1A is a diagrammatic side view representation of a sensor according to the present invention.

FIG. 1B is a diagrammatic enlarged view of a portion of the sensor of FIG. 1A.

FIG. 1C is a diagrammatic representation of the operation of the sensor of FIG. 1A.

FIG. 2A is a diagrammatic top view of a sensor device.

FIG. 2B is a diagrammatic enlarged view of a portion of the sensor device of FIG. 2B.

FIG. 2C is a diagrammatic view of the sensor of FIG. 2A without any beads in the sensor channel.

FIG. 3 graphically illustrates the reproducibility of potential versus time (E vs t) transients due to spectator species diffusion in a sensor channel.

FIG. 4 is a diagrammatic representation of the operation of a sensor in accordance with another embodiment of the present invention.

DETAILED DESCRIPTION

Figure 5:
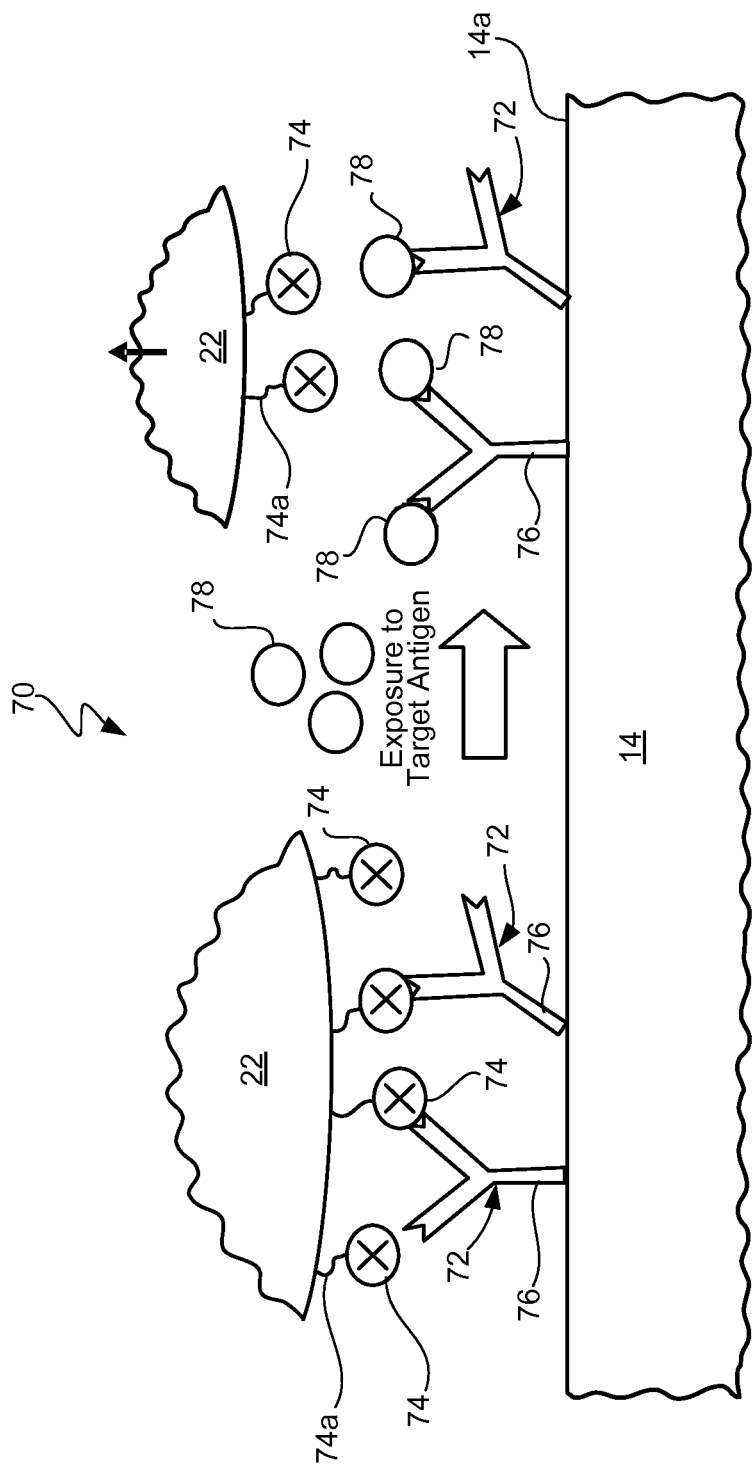
FIG. 5 is a diagrammatic representation of the operation of a sensor in accordance with yet another embodiment of the present invention.

Reference will now be made in detail to some specific embodiments of the invention including the best modes contemplated by the inventor for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. For example, the techniques of the present invention will be described in the context of a glass-based electrochemical sensor, although other materials, such as plastics and polymers, could also be used.

In the following description, numerous specific details are set forth in order to provide a thorough understanding of the present invention. The present invention may be practiced without some or all of these specific details. In other instances, well known process operations have not been described in detail in order not to unnecessarily obscure the present invention.

As shown in FIGS. 1A and 1B, a sensor 10 includes an upper plate or membrane 12 spaced from a lower plate or membrane 14 to form a channel 16. A first electrode 18 is located at one end of the channel, and a second electrode 20 is located at an opposite end of the channel. The distance between the electrodes is (g). The electrodes have a length (l). (See FIG. 2A).

The electrode 18 is a generator electrode. It generates a spectator species, for example, chloride ions, that diffuse in an aqueous solution in the channel 16, and which do not chemically interact with the any chemical species in the channel. The spectator species are generated at a constant rate galvanostically. In other words, to generate spectator species such as chloride, a constant current pulse is applied to the generator electrode.

The second electrode 20 is a sensor electrode that potentiometrically monitors the arrival rate of the spectator species. It is thus configured to detect the concentration of the spectator species at its end of the channel, after the spectator species has traveled along the channel from the generator electrode to the sensor electrode.

Both electrodes may be formed on, as shown, an inner surface 14a of the lower plate 14. Alternatively, the electrodes could be fabricated on an inner surface 12a of the upper plate 12. As discussed below, the sensor would also include appropriate counter and reference electrodes.

The channel is populated by a plurality of beads or microbeads 22. The beads also act as spacers in the channel between the top plate 12 and the bottom plate 14. Alternatively, spacer dots, as discussed below, may be used to space the upper plate 12 from the lower surface 14. The beads may be spherical in shape. Other shapes, however, are also possible. For instance, the beads may be cubical in shape.

The beads are attached to a surface of the channel by a molecular tether (molecular bridge) involving the target substance (for example, ssDNA or antigen). The molecular tether can be cleaved (broken) in the presence of a target substance that the sensor is designed to detect. As shown in FIG. 1B, for example, the beads may be attached to the inner surface 14a of the bottom surface 14 by a number of DNA (deoxyribonucleic acid) tethers 24.

The tethers 24, in one embodiment, are formed by the hybridization of two single-strand DNA (ssDNA) fragments. As is known, DNA hybridization occurs when a single-stranded DNA of a particular sequence of nucleotide bases interacts with a "Watson-Crick" complementary strand of a ssDNA, resulting in the formation of a hybrid, double stranded DNA (dsDNA) molecule. One fragment 24a, in the presently-described embodiment, is initially attached to the surface 14a of the membrane 14 in the gap between the generator electrode 18 and the sensor electrode 20. The sequence of this ssDNA fragment is selected to be complementary to the target ssDNA, that is, the DNA to be detected by the sensor. The second, shorter ssDNA fragment 24b is attached to the surface of the bead 22. The number of hybridized tethers linking each bead to the channel surface 14a is controlled by the surface density of the two components. The high bead density shown in FIG. 1A corresponds to the desired initial state of the sensor.

The functioning of the sensor involves two independent elements: recognition of a specific sequence of the target DNA, for example, and a signal transduction function. The signal transduction function involves measurements of the rate of diffusion of the spectator species along the channel in the inter-electrode gap, the gap between the electrodes 18 and 20. The length of this gap, as noted, is (g). The diffusion of the non-interacting spectator species is monitored by recording potential versus time (E vs t) transients at the potentiometric sensor electrode 20. The rise time and the shape of the transients depend on the free volume of the solution in the channel between the generator electrode 18 and the sensor electrode 20, and thus on the number and density of the micro-beads in the channel.

The E vs t transient recorded in the initial state of the sensor is expected to exhibit a rapid rise of potential at the sensor electrode 20 due to a rapid diffusion of the spectator species through the relatively small free volume in the channel. The latter can be computed by subtracting the volume of the beads from the total volume of solution in the channel. The theoretical expectation of the functional dependent of the measured sensor's potential on time is available by solving Fick's equation of diffusion. The concentration of the spectator species versus time at the sensor electrode, a distance (g) from the generator electrode, C(g, t), obeys the following equation obtained by solving Fick's law of diffusion:

$$C(g, t) = C_{in} + \frac{i}{nF\rho AD}\left\{2\left(\frac{Dt}{\pi}\right)^{1/2}\exp\left(-\frac{g^2}{4Dt}\right) - g\cdot erfc\left[\frac{g}{2(Dt)^{1/2}}\right]\right\} \quad (1)$$

where $C_{in}$ is the initial, background spectator species; A is the cross-sectional area of the channel (a product of the channel height (h) and the length of the electrodes (l)); $\rho$ is a fractional free volume of the channel; D is the diffusion constant of spectator species; i is the magnitude of the current used to generate the spectator species; n is the number of electrons involved in the elementary generation reaction; and F is the Faraday constant (approximately 96,500 C/mol).

The inter-electrode gap (g) may be between about 10 and 50 microns (um). Spherical beads may have a diameter of approximately 2-5 microns and a density of about 2.5 g/cm$^3$. The thickness or height of the channel (h) is determined by the diameter of the beads, and/or spacers of the same height. Thus, for a 2 micron bead, (h) would be equal to approximately 2 microns. The length of the electrodes (l) may be between about 50 and 1,000 microns. The diffusion of the spectator species between the generator and sensor electrodes is linear as the channel height is much less than its length (h<<g).

The plates 12 and 14 may be made of an electrically insulating glass, such as microscope slides. Alternatively, the plates may be made of other smooth, electrically insulating materials such as a silicon dioxide-coated silicon wafer, sapphire or certain ceramic and polymer materials. The micro-beads may be made of an inert material such as borosilicate glass. The beads may also be made of other materials such as latex and silicon dioxide.

The electrodes may be photolithographically fabricated on the membrane 14. The generator electrode 18 is made of thin gold film over-coated with silver and a silver-chloride (AgCl) film. Chloride ions (Cl$^-$) are thus generated as the spectator species by the application of a negative (reducing) current pulse to the generator electrode. The active layer of the sensor electrode 20 is also silver/silver-chloride (Ag/AgCl).

The diffusion of the chloride ions is monitored by recording the E vs t transients at the sensor electrode 20. The rise and the shape of the transients, as noted, depend on the free volume of the solution in the channel between the generator electrode 18 and the sensor electrode 20. The rate of diffusion of the spectator species in the inter-electrode gap is thus used to measure the population density of the beads 22 in the channel 16.

To incorporate the DNA recognition element of the sensor, the ssDNA strands 24a (the probe ssDNA) complementary to the target DNA are chemically bound to the channel surface in the inter-electrode gap. They are used as molecular tethers immobilizing the individual beads in the channel 16. Each bead is attached to the device surface by a small number (as low as one) of the dsDNA tethers 24.

As represented by FIG. 1C, the DNA sensing process involves competitive hybridization between the surface bound ssDNA fragment 24a in the inter-electrode gap and the target DNA 25. This involves breaking or dehybridization of the dsDNA tether and results in the release of at least some of the micro-beads. This is possible since the original tether attaching the beads consists of a shorter section of the dsDNA than the one formed during the sensing process.

Following the initial recording of the E vs t transient, the top plate 12 of the device is removed and a small volume (as small as 1 mL) of an analyte or sample solution is placed on the surface of the channel 16 and then equilibrated. This could involve a period of 5 to 60 minutes and a slightly increased temperature above room temperature. Presence of the target DNA in the analyte solution will result in its hybridization with the complementary surface bound DNA 24a, as mentioned above. This will result in a release of at least some of the beads from the surface 14a of the plate 14. The term release means a complete release of a bead from a channel surface. In some cases, not all the tethers joining a bead to a channel surface will be broken. However, in other cases, this will occur. In either case, the free volume of the analyte solution in the channel will be increased.

Consequently, a second measurement of the spectator species diffusion in an aqueous solution in the channel, carried out after rinsing the surface of the device (channel) and replacing the top plate to recreate the channel, will accurately report the difference, if any, in the population of the beads in the channel. The rinsing step is designed to a) rinse away the micro-beads that are no longer tethered to the device surface, b) to remove the analyte sample and thus to terminate the incubation process and c) to establish the exact and desired base concentration of the spectator chloride ions in the channel. (See Equation 1). The second measurement will measure the new population density of the micro-beads in the channel. If the latter is smaller than the initial than this indicates that the specific, target ssDNA was present in the analyte. By quantitatively comparing such measurements with the set of control experiments done with known concentrations of dsDNA (sensor calibration), one can also deduce the concentration of the specific ssDNA in the sample.

The top plate 12 may be removably secured to the channel sidewalls. As such, the plate 12 may simply be lifted up to introduce a solution into the channel. Alternatively, the plate 12 may be fixed to the channel sidewalls, and the plate would include inlet and outlet ports for the introduction and removal of an analyte solution and of the released beads. This would require that the top plate have two positions: higher and lower so that the beads, should they become released, could then be washed away. Suitable microfluidic control mechanisms such as valves, pumps and routers could be used to introduce and remove a solution from the channel.

The inter-electrode gap may also include electrically-conductive pads (not shown) located between the generator electrode 18 and the sensor electrode 20. These pads may be formed by evaporating gold on one or both of the surfaces 12 and 14. The pads would not be in electrical contact with either the generator or sensor electrode, but would function as independent electrodes. Thus, the pads should be no closer than about 1 micrometer to either the sensor or generator electrode. These pads would be used if it were necessary to bind different types of ssDNA to different devices of a larger array of sensors. The sensor 10, as discussed below (see also FIG. 2A), would also include an additional counterelectrode (described below). A common reference electrode would be involved in applying and controlling the potential of the pad with an auxiliary potentiostat (not shown).

The sensor 10, as discussed below, includes a reference electrode and a counterelectrode. A potentiostat (now shown) is used to provide a desired potential relative to the reference electrode. The counterelectrode closes the potentiostatic circuit.

As shown in FIGS. 2A, 2B and 2C, a sensor device 40 includes a parallel array of electrodes. Specifically, the sensor device 40 includes a central generator electrode 18a positioned between two sensor electrodes 20a and 20b. The generator electrode is located at the juncture of the channels 16a and 16b of the device. The inter-electrode gap (g) between the generator electrode 18a and sensor electrode 20a can be the same as that between the generator electrode 18a and the sensor electrode 20b. As such, the generator electrode is symmetrically positioned between the two sensor electrodes.

The target substance introduced into the channel 16a may be the same as the target substance introduced into the channel 16b. Alternatively, the target substance in the respective channels may be different.

The sensor device 40, in this latter configuration, is designed to simultaneously detect different target substances such as different ssDNA fragments of specific sequences. The biological binding mechanism or tether in the respective channels would also be different. Therefore, the DNA tethers are selected to be complementary to the different target DNAs.

The sensor device 40 further includes two counterelectrodes 42 and 44. These electrodes are two symmetric, externally shorted bars. They assure an even current distribution. A reference electrode 46 is also part of the sensor 40.

As discussed, a galvanostat is used to apply a constant current between the generator 18a and counterelectrodes 42, 44. In addition, in order to apply potential to the inter-electrode pads, if present, an auxiliary potentiostatic circuit would be used. It would consist of the pad, functioning as a working electrode, and an additional counterelectrode (not shown in FIG. 2A). The common reference electrode 46 would be used to complete the potentiostatic circuit. The potential of each pad of the array of sensors would be independently controlled. A pad, however, and its counter and reference electrodes need not be positioned in any specific way relative to each other. This is because that circuit would not pass essentially any current. As mentioned above, one reference electrode could function for both circuits of the generator electrode and the conductive pad.

The sensor and generator electrodes are photolithographically fabricated using gold on a glass substrate. The electrodes may be fabricated by electroplating of silver followed by its partial oxidation to AgCl in a KCl electrolyte. The reference and counter electrodes can also be photolithographically fabricated. The area 48 (the diagonally hatched pattern) is coated with an insulator, such as a polymer, to determine the length (l) of the generator and sensor electrodes. The dotted line rectangular area 50 marks the area enclosed by the upper plate 12. FIG. 2B illustrates the beads 22 attached to the channel surface in the inter-electrode gap. FIG. 2C shows the channel without the beads.

The beads, as noted, may act as spacers between the upper and lower surfaces of the sensor. Alternatively, spacer dots, for example, polymer spacers, may be lithographically deposited at the corners of the upper or cover plate 12. The thickness of the spacers may be approximately equal to, for instance, the diameter of a spherical bead. A mechanical squeezing device can be used to assemble the sensor device.

The sensor device 40 includes two channels, and the associated sensor and generator electrodes. It is also possible to construct a device that has more than two channels along with the necessary sensor and generator electrodes for testing whether the analyte solution contains more than two specific ssDNA fragments.

An array of sensors includes an ensemble of individual sensors described above. Each sensor would include generator and sensor electrodes, each having their own inter-electrode gap, either including or not including electrically-conductive pads. The purpose of such an array would be to contain a large number of sensors in one hand-held device which when exposed to one aliquot of a sample would simultaneously indicate the presence of several target compounds of interest.

As shown in FIG. 3, the E vs t transients due to chloride ion (Cl⁻) diffusion are reproducible. Specifically, three sets of chloride ion Electrochemical Time-of-Flight (ETOF) experiments (points) and three fits of Equation 1 to the data using channel thickness (h) as the adjustable parameter (lines) are illustrated. The experiments were done with a device like that of FIG. 2A wherein g=50 µm, the average height h=3.09 µm, i=1.0 µA, $[Cl^-]_{init}$=1.00 mM, and $D_{Cl^-}$=1.90×10⁻⁵ cm²/s. However, the channels did not contain any beads. (See FIG. 2C).

The sensor response (E vs t) can be obtained using the Nernst equation with the experimentally obtained slope value. Using 50 µm gap (g) devices with 3.1 µm thickness (h), a good agreement between the theory and experiment was obtained, as shown in FIG. 3, for Cl⁻ diffusion. To document reproducibility of the device assembly, three transients obtained in three separate experiments are shown involving repetitive opening and reassembling of the device 40. The average thickness of the channel obtained by fitting h as the variable is 3.09±0.02 µm (±0.6%). The rate of Cl⁻ generation can be varied in the range 0.01-1 µmol/s ($i_{gen}$=1-100 mA/cm²). The lower limit is set by the maximum time of 1 ms allowed for the double-layer charging of the generator electrode.

There exist numerous well developed procedures for binding ssDNA to glass and other solid surfaces. For example, one strategy relies on biotin-streptavidin binding. In the first step, glass beads are exposed to a solution of bovine serum albumin (BSA), a protein known to strongly and irreversibly bind to glass surfaces forming a monolayer coating. Inclusion of a controlled fraction of biotinylated BSA will allow control over the coverage of streptavidin and consequently the ssDNA. Five'-biotinylated DNA strands of the type 5'-biotin-$(dT)_{10}$-TGT GCT AGT ACA GAC-3' (SEQ. ID No. 1) can be used. The 10 thymine segment functions as a spacer group. The fifteen bases "recognition" segment can be used to bind the beads to the probe DNA on the device surface. The 25 bases probe DNA can be attached to the gold coated inter-electrode surface, assuming gold pads are present in the inter-electrode gap, via thiol chemisorption. This strategy, as opposed to BSA adsorption, is chosen for two reasons. BSA adsorption might interfere with the micro-electrode functioning. Furthermore, the ability to independently control the potential of the gold pads in the inter-electrode gap will be essential in the preparation of the micro-array devices where individual units will carry different probe DNA strands. Chemisorption of thiol DNA derivatives such as 5'HS-$(CH_2)_6$-AGA TCA GTG CGT CTG TAC TAG CAC A-3' (SEQ. ID NO. 2) is impeded at high negative potentials. Therefore, keeping just one unit of an array at open circuit and the rest at about −1.1V will direct assembly of a particular probe DNA onto a single, selected inter-electrode pad. The last 15 bases of the probe DNA are complimentary to the terminal 15 bases of the biotinylated bead DNA. The complementary target ssDNA may be between 15 and 25 bases long. All custom synthesized ssDNA samples are commercially available.

The number of DNA tethers that can be formed between a single bead and the device surface depends on the surface concentration of the ssDNA fragments, the length of a tether and the radius of the bead. The latter determines the curvature of the bead surface. Relying on a purely geometric argument, the area (S) of a spherical cap of height t (equal to the average length of a DNA tether) is S=2πRt; if t is estimated to be 10 nm, then S=6.3×10⁻¹⁰ cm². The maximum surface density of the attached ssDNA chains on glass beads is limited by the size of BSA (about 44 nm²/molecule; streptavidin is smaller, assuming binding of one ssDNA per biotinylated BSA). This gives 2.3×10¹² molecules/cm². An estimate of the maximum coverage of about 2×10¹² molecules/cm² can be used as the maximum surface density of the double-stranded tethers. This, combined with the contact surface area S, yields 1000 as an estimate of the maximum number of tethers.

The force required to break or "melt" a double-stranded DNA tether is known from the art describing single DNA molecule "stretching" methods such as "magnetic beads", "laser tweezers" approaches and atomic force microscopy. These measurements offer insight into the elastic and inelastic regimes encountered in such single molecule stretching and "unzipping". In the latter case, when a 5' and 3' terminals of a double helix at one end of a DNA molecule are pulled apart, the forces are about 10-15 pN (pico-Newtons) and correspond to stepwise breaking of individual base pairs (thus unzipping). When the opposite ends of a dsDNA are pooled, the so called overstretching transition (also referred to as dsDNA melting transition) is observed in the 65 to 200 pN range. Much larger forces are involved in breaking a covalent bond within dsDNA. For example, a single molecule of dsDNA was broken by a receding meniscus method at a force of 960±140 pN.

In the sensor of the present invention, forces on the order of 100 pN will likely be required to break a single tether. Thus, a bead attachment by even a single dsDNA tether is likely a sufficiently strong attachment to resist rinsing, thereby preventing false positive readings.

The DNA surface density on glass beads can be determined by epi-fluorescence microscopy. Following DNA binding via the BSA/streptavidin scheme, the beads can be treated with a fluorescently labeled ssDNA reagent such as OliGreen (Molecular Probes Inc.). The goal is to control the binding density in the range of about 2×10¹²-2×10⁹ molecules/cm². This spans the range of the attachment densities from a high of 1000 tethers per bead to one tether per bead. In the latter case, a single bead would carry only about 200 DNA strands (and thus fluorophores). Nevertheless, these measurements are well within the sensitivity of the fluorescence microscope equipped with a cooled CCD camera. The surface density of the DNA strands on gold will be measured using a chrono-coulometric procedure. It involves saturation binding of ruthenium hexamine to the DNA phosphate groups. Precise DNA surface density is obtained from the intercepts of the Anson plots after the double-layer capacitance charge subtraction. Sensitivity of these measurements extends to about 1×10¹² molecules/cm². Clearly, in order to control the number of dsDNA tethers binding individual beads to the gold surface, the DNA binding density on the beads will need to be controlled via control of the mole fraction of the biotinylated BSA in the BSA solutions.

Following incubation of the DNA derivatized device surface with a suspension of the DNA derivatized beads and rinsing, the bead surface density can be determined by optical microscopy. Determination of the number of tethers attaching each bead is far more challenging. However, it does not exceed the sensitivity of fluorescence microscopy with a thermoelectrically cooled CCD camera. One approach is to rely on dimeric cyanine dyes (such as YOYO-1 characterized by and available from Molecular Probes Inc.) specifically developed to stain dsDNA. These dyes are known to fluoresce only after intercalating into dsDNA. To avoid quenching, gold surfaces must not be used in these measurements. Instead, probe DNA can be bound to glass surfaces via biotin-streptavidin protocol. This will not significantly alter the number of tethers per bead as long as that number is determined by the smaller surface density of the ssDNA on the beads.

The response of the chloride ETOF devices loaded with the beads needs to be calibrated. Since regardless of the bead attachment density the system is always above percolation threshold, the shape of E v t transients can be quantitatively predicted knowing the number of the beads in the inter-electrode gap and the dimensions of the diffusion channel. Thus, the effective porosity or void-volume fraction ($\rho$, see Equation 1) can be calculated and compared with the experimental results. Any discrepancy between the experiment and the calculations would most likely be due to the difference between the nominal and actual bead size or due to bead size dispersion. In either case, these experiments will allow for the calculation of the average bead diameter to be used in the subsequent DNA sensing measurements.

The sensor should be highly sensitive and have a reasonable response time, for instance, on the order of about 10-30 min. As discussed, target DNA sensing involves recording two E v t transients, before and after exposure of the sensor to a DNA sample. Following sensor calibration, the top plate of the sensor can be removed and a small volume of a sample solution carrying the target DNA deposited onto the sensing surface. Following incubation and rinsing, the top plate is reassembled and the E v t transient recorded.

The sensitivity of the sensor depends on a number of variables, including the concentration of the target DNA and the length of the target DNA sequence. As discussed, the beads are attached via DNA tethers. Each tether may contain a 15-base double-strand. The probe-DNA may be 25 bases long. The length of the complimentary target DNA may be varied between 15 and 25 bases, to optimize sensitivity. In view of the small size of an individual inter-electrode gap area, the volume of the sample solution could be exceedingly small (for example, about 1 mL). The sample solution should also carry a known chloride ion concentration (about $1.0 \times 10^{-4}$ M). The later is an input parameter in the interpretation of the ETOF transients (see Equation 1). Temperature and incubation time are also naturally important parameters to control.

Detection of the competitive probe-target DNA hybridization requires release of at least one bead. This in turn requires dissociation of all dsDNA tethers linking a bead to the surface of the device. Due to the constrained space between a bead and the device surface, the sensitivity of the sensor most probably is inversely related to the number of tethers binding individual beads.

A variable pressure flow cell can be used to develop a controlled way of rinsing the device surface to remove the unattached beads following probe-target DNA hybridization. It will allow control over the water flow velocity and thus the hydrodynamic force acting on the beads attached to the cell's surface. Briefly, such a cell may consist of two parallel glass plates (about $2 \times 10 \text{ cm}^2$) separated by a distance w=20-50 µm. In addition to this parallel plate narrow slit element, the flow system can include a pump, a buffer reservoir and a flow meter. The maximum water (buffer solution) velocity ($v_{max}$) that still corresponds to laminar flow conditions can be calculated from the critical value of a Reynolds number, Re≤100 for the narrow slit cell. Re=$w\rho v_{max}/\mu$, where $\rho$ and $\mu$ are water density and viscosity. $V_{max}$ may approximately equal 100 cm/s. Such flow will require a hydrostatic pressure ($\Delta P$) of 4 bar (calculated using $\Delta P = 8\mu L v_{max}/w^2$, where L=10 cm, the length of the cell). Flow velocity of this magnitude would exert a force $F_{max}$ of 1 nN (nano-Newton) on a 2 µm bead attached to one of the plates of the cell. The estimate of the critical Reynolds number is rather conservative. It is likely that 5 to 10 times larger hydrodynamic forces can be generated with this flow system. This simple apparatus will allow microscopic observation of the release of the beads following incubation with a target DNA sample solution, as well as an assessment of the minimum force required to detach the beads. Note that the estimate of the force required to "melt" a single dsDNA tether of about 65-200 pN is well within the force range of this flow cell apparatus. Therefore, a distinction should be able to be made between beads attached by 1 to 10 tethers just by controlling buffer flow velocity in the parallel plate cell and relating it to the hydrodynamic force required for detachment. This capability will be important in the process of optimizing sensor sensitivity. The estimates of the hydrodynamic forces in the flow cell also work under the conditions of low surface densities of the beads.

The smallest number of detached beads that can be detected depends on several design parameters. In view of Equation 1, it is clear that the sensor response is sensitive to the changes of the fractional free-volume (or permeability $\rho$) in the channel. Changes on the order of 5-10% can be easily detected visually. To optimize sensitivity, the device size can be minimized and thus the total number of the beads in the inter-electrode gap is minimized. To increase sensitivity, it is also possible to use micro-beads larger than 2 µm in diameter.

A more precise and practical approach to obtain channel permeability (and thus bead density) relies on the measurements of transit times, $\tau$, defined as time passed between the application of the current pulse and the sensor potential reaching a value, for example, 50 mV or 70 mV negative relative to its initial value. From calculated E v t transients, it is known that $\tau$ depends linearly on $\rho$. Thus, the precision of the measurement of the bead density will depend on a) the definition of $\tau$, b) the noise level in the E vs t recordings and c) the precision of the device assembly. The latter is less than 1%

The measurements of sensor potential are also of high precision (low noise) and the fact that an absolute level measurements is not required is also an advantage. Altogether, it is expected that a 1% precision in signal transduction will be achieved. This corresponds to detection of a single bead detachment.

While the above assessment of sensor sensitivity with respect to the bead population is straightforward, it is more difficult to predict sensor sensitivity with respect to the concentration of the target DNA. To achieve and to accurately measure very low detection limits, on the order of low pico-molar (pM, or $10^{-12}$ M) or femto-molar (fM, or $10^{-15}$ M), the surface concentration of the probe DNA in the inter-electrode gap should be decreased to limit sequestering of the target DNA unrelated to the competitive hybridization and bead release.

The sensitivity of the sensor will depend on a number of parameters relating to the device design and to the equilibria involved in the competitive hybridization between the target and probe DNA strands. These are expected to depend on the difference in the number of complimentary bases in the probe-target double-strand and in the ssDNA segment linking the beads to the surface. In any given case, it is expected that the sensor will exhibit an on/off type behavior (detachment of all the beads) when exposed to samples of complimentary target DNA with concentrations well above the detection limit. In the concentration range approaching the detection limit, it is expected that a fraction of the beads will be detached. The detection limit could be sub-pM. Most importantly, it may depend on and improve with the decreasing number of dsDNA tethers liking individual micro-beads to the device surface. The key advantage of the ETOF signal transduction mechanism, in addition to the fact that it will require only simple electronic measurement circuit, is its intrinsic sensitivity. It could ultimately allow detection of single molecule events by transducing breaking of a dsDNA tether into a detachment of a bead deduced by measurements of the time required to observe a specific change of a sensor potential.

A number of implementations and techniques have been described. However, it will be understood that various modifications may be made to the described components and techniques. For example, advantageous results still could be achieved if steps of the disclosed techniques were performed in a different order, or if components in the disclosed device are combined in a different manner, or replaced or supplemented by other components.

For example, other biological binding and cleaving events, such as competitive antigen-antibody recognition or enzymatic cleaving of a specific peptide sequence, can be relied on as the process responsible for the selective recognition of a target substance, triggering the release of a surface-bound bead.

For instance, as shown in FIG. 4, a sensor 60 uses a number of antibody-antigen-antibody tethers to attach the beads 22 to a sensor surface 14a. The sensor is designed to respond to a particular antigen 62. The tethers 64 consist of a sandwich of two antibodies 66a and 66b (represented by Y-like symbols), and two antigen molecules 62 bridging the antibodies. In this type of a sensor, two different monoclonal antibodies (one bound to a sensor surface 14a and the other to a surface of a bead 22) could be used, each targeting a different epitope of the antigen. Alternatively, a combination of a monoclonal and polyclonal antibody, or just one polyclonal antibody attached to both the bead and device surfaces can also be used. The scheme of competitive antibody antigen interaction (proceeding from left to right in the figure) involves an assumption of facile kinetics of the antigen-antibody dissociation. A reverse scheme in which the target antigen recognition step involves micro-bead attachment to the device surface can also be implemented as described below.

An example of a target immunogen is free prostate-specific antigen (PSA). In view of the importance of sensitive and specific detection of PSA in the early detection of prostate and breast cancer, the rational of this selection is apparent. In this case, monoclonal PSA antibodies (mAnti-PSA) will be first attached to the device surface and saturated with PSA. The bead attachment will involve exposure of the device surface to a suspension of micro-beads carrying polyclonal PSA antibodies (pAnti-PSA) on their surface. As in the DNA case, the sensing process will involve competitive antibody-antigen interactions between PSA in the analyte solution with mAnti-PSA-PSA-pAnti-PSA tethers leading to the release of the micro-beads.

Additionally, in yet another embodiment, a sensor includes an antigen-antibody complex comprising a modified antigen exhibiting a lower binding constant than the native antigen. The sensor relies on breaking or cleaving of this pre-established antigen-antibody complex via competitive interactions with an analyte, the native antigen. This will result in a free energy driving force of the exchange step. The sensor uses the dissociation of the antigen-antibody complex both as a way of achieving sensor selectivity and specificity, and as its signal transduction mechanism.

As shown in FIG. 5, such a sensor 70 includes a number of microspheres 22 bound to a sensor surface 14a by a number of molecular tethers 72 incorporating a modified antigen-antibody complex. The tethers 72 include a modified antigen 74 and an antibody 76. The antigen 74 has a lower binding constant than a native or target antigen 78. The antibody molecules 76 are initially immobilized on the device surface 14a while the modified antigen protein 74 is attached to the surface of the micro-spheres 22 by, for example, a molecular spacer or linker 74a. Formation of the antibody-antigen complex 72 links the micro-spheres to the device surface. This sets the initial, active state of the sensor.

The analysis step involves exposure of the sensor device to a volume, for example, of a sample solution. If the latter contains a targeted immunogenic protein its interactions with the sensor's antigen-antibody complex during an incubation period results in the exchange of the antigens and the breaking of a tether 72.

Two conditions are required to make this scheme practical: the exchange interactions between the original antigen-antibody complex and the analyte antigen must be energetically favorable as well as kinetically facile. The use of a modified antigen with an approximately 2 orders of magnitude lower binding constant than a target antigen will meet both requirements. Such modification will not only make the exchange equilibria with the analyte antigen thermodynamically favorable, but it will also improve the exchange kinetics. Knowing that $K=k_{on}/k_{off}$ ($K$ is the equilibrium constant or binding constant of the antibody-antigen complex, $k_{on}$ is the binding rate constant, and $k_{off}$ is the dissociation rate constant), surface modification of the antigen will result in an increase of the dissociation rate constant. Thus, following a simple rinse, breakage of all tethers holding a micro-bead can be easily detected with an optical microscope. Alternatively, the release of micro-spheres can be used to generate an electrical signal. Another approach relies on paramagnetic micro-spheres or beads; their detachment in a magnetic field generated by a stack of small permanent magnets circumvents the rinsing step. The general design of this approach is shown in FIG. 6.

Figure 6:
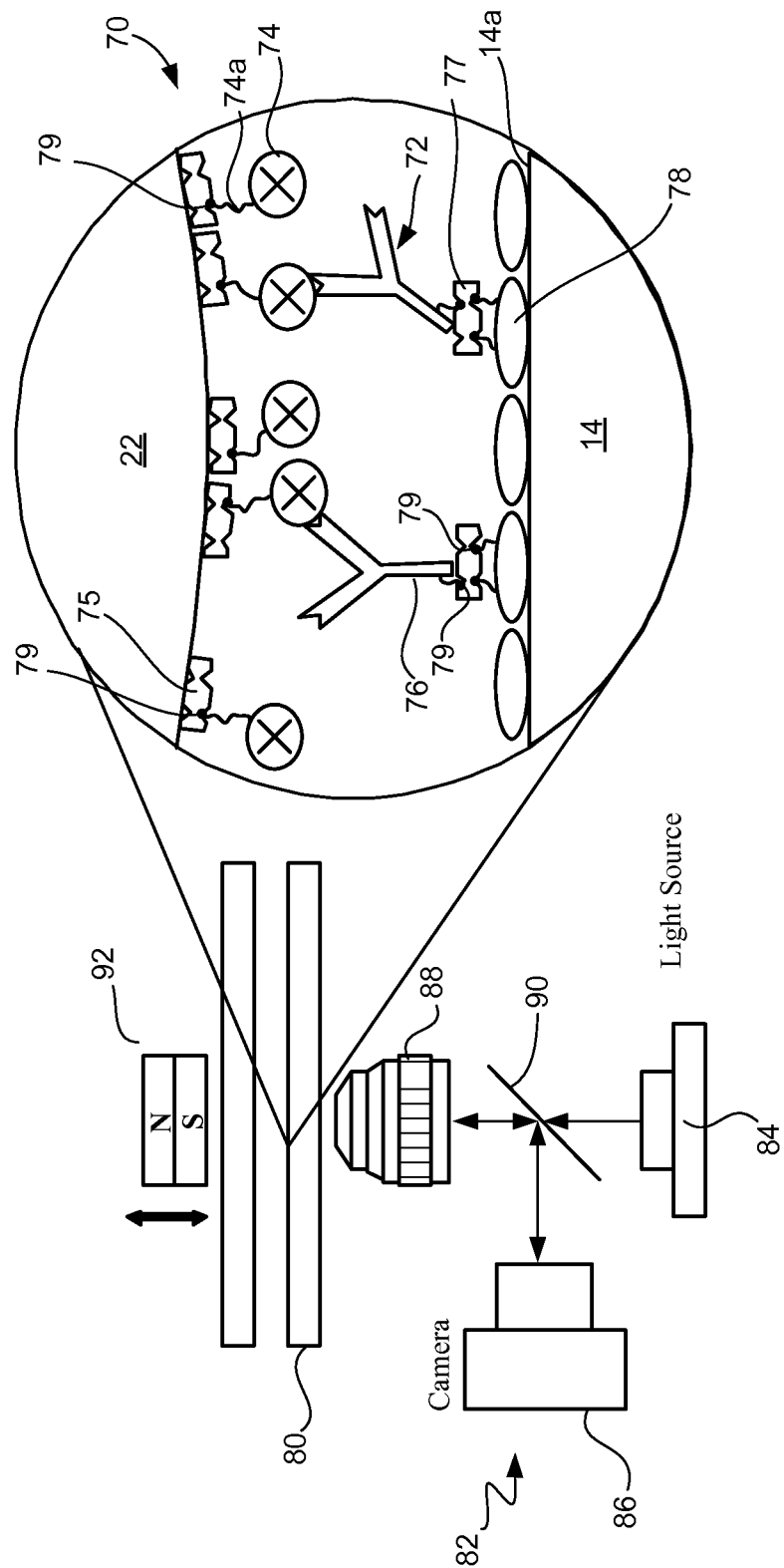
FIG. 6 is a diagrammatic representation of a system to monitor micro-bead detachment.

As shown in FIG. 6, the sensor 70 is positioned on a stage 80 of an inverted microscope assembly 82. The microscope assembly 82 includes a light source 84 and a charged coupled device (CCD) camera 86. Light from the light source is directed to an optics portion 88 of the microscope assembly via a transreflector 90. The camera 86 also views the optics 88 by way of the transreflector. A stack or group of permanent magnets 92 is located above the sensor 70. The position of the magnets is selected to generate a desired magnetic force on the paramagnetic beads 22.

The tethers 72, in one embodiment, may include a modified PSA antigen molecule 74 and a PSA antibody 76. The target antigen 78 is also PSA. The molecular linker or spacer 74a may be attached to a bead 22 via a streptavidin protein 75. The antibody 76 is also attached to the sensor surface 14a via a streptavidin protein 77 and a protein 78, such as BSA, that is used to coat non-biological surfaces. BSA, as noted, strongly absorbs on glass, plastic or other surfaces.

One attachment scheme involves commercially-available, for example, from Bangslabs or Dynabeads paramagnetic, streptavidin-coated beads. Next PSA is biotinylated. This can be easily accomplished, for example, by treating it with one of any number of NHS-biotin derivatives, including molecules with spacer groups between the hydroxysuccinimide and biotinyl ends of the molecule for easier binding, and the hydroxysulfo-groups allow the reactants to all be water soluble. An additional factor encouraging the use of molecular spacers is that multiple bonds holding micro-spheres together increase the strength of the tether only when the antigen molecule is placed at the end of a spacer group. The amount of PSA attached to the beads may be measured using fluorescently labeled PSA and epi-fluorescence microscopy. Standard streptavidin-biotin complex formation is used. This is shown in FIG. 6 where the streptavidin protein 75 is adsorbed at the upper bead surface. Biotin is a very small molecule in comparison. It is symbolized by a dot 79 in one of the four docking grooves of the streptavidin protein 75 or 77.

To consider the sensitivity of a sensor, reference is again made to FIG. 5. The active surface of an individual sensor may comprise an area of approximately 50×50 μm². Thus, an area of 1 mm² may contain an array of 100 or more individual micro-sensors each designed to detect a specific protein or a DNA sequence. The active area of each sensor may be populated by a random array of approximately 100 micro-beads (about 1 μm in radius). Each micro-bead may be attached to the device surface by approximately 100 or fewer molecular tethers each involving a complex between a modified antigen and its specific antibody or a dsDNA.

The expected high sensitivity of the sensor derives from two factors intrinsic to its design. First, the signal transduction (involving either optical microscopy or generation of electrical signal) incorporates an intrinsic amplification element in that a small number of single molecule events (dissociation of the molecular tethers) result in an easily detectable macroscopic event—detachment of a relatively large particle. The second factor concerns the antigen exchange reaction. The latter can be represented by:

$$Ab\text{-}Ag' + Ag \rightarrow Ab\text{-}Ag + Ag' \quad (2)$$

where Ab represents antibody, and Ag' and Ag represent the modified and native or unmodified antigen protein, respectively. It is important to note that the each exchange equilibrium involves an immobilized Ab-Ag' complex and an Ag protein both confined within a small reaction volume between the surfaces of the micro-bead and the sensor surface. Due to this confinement effect, reaction or equation (2) can be considered to be a unimolecular process. This then leads to:

$$K_e = \frac{p}{1-p}$$

and thus:

$$p = \frac{K_e}{1 + K_e} \quad (3)$$

where $K_e$ is the equilibrium constant of reaction (2), and p is the probability of a successful exchange (breaking of a tether). In macroscopic terms, the latter is synonymous with the reacting fraction of the initial population of Ab-Ag'+Ag in the confined reaction volume. Naturally, $K_e$ is simply the ratio of the binding constants of the native (K) and modified (K') antigen: $K_e = K/K'$. A surface modification of an antigen protein can result in at least two orders of magnitude decrease of its binding constant yielding p of 0.99. In thermodynamic terms, the "confinement effect" refers to the entropy of mixing which is not a component of the free energy of reaction (2) when the latter takes place in a reaction volume much smaller than K or K'. Next the question is asked: how different is p if equilibrium or reaction (2) is considered in a classical "non-confined" system? Then, the relationship between p and $K_e$ is straightforward:

$$K_e = \frac{p^2}{(1-p)^2} \quad (4)$$

This yields p=0.91 for $K_e$ of 100. Therefore, whether the confinement effect is significant, it is concluded that essentially every encounter between an analyte antigen and a modified antigen-antibody complex will result in its dissociation. In other words, when $K_e$ is about 100 or greater, reaction (2) becomes nearly irreversible. Naturally, this thermodynamic argument must be broadened by considering the kinetics of the exchange and specifically the magnitude of the dissociation rate constant, $k_{off}$. The latter can be estimated assuming that the binding rate constant, $k_{on}$, is diffusion limited. Its magnitude is about $10^7$-$10^8$ M$^{-1}$ s$^{-1}$. The latter is based on the fact that the rate constant of bimolecular collisions of the molecules diffusing with a diffusion constant (D) of about $10^{-6}$ cm²/s is about $10^9$ M$^{-1}$ s$^{-1}$, and that only about 1-10% of those collisions are fruitful. As mentioned above, a decrease of K by two orders of magnitude puts its upper bound value at about $10^{10}$ M$^{-1}$. Therefore, the dissociation rate constant can be expected to be greater than $10^{-3}$-$10^{-2}$ s$^{-1}$. In the case of PSA, for example, which exhibits K values of about $10^9$ M$^{-1}$, the $k_{off}$ (following PSA modification) is expected to be 1-10 s$^{-1}$.[11] These values do not forecast a need for excessively long equilibration times in order to comply with the exchange kinetics. Thus overall, a crucial postulate is arrived at that within this set of constraints the sensor will act as an integrating device, as each antigen that reacts with and breaks a tether is effectively trapped for the duration of the experiment. Therefore, sensor sensitivity is expected to be a time-dependent function since in the range of low analyte concentrations, the sensor's response will become diffusion controlled. Heretofore, no existing immunoassay method has exhibited this property.

To expand on this unique characteristic, the sensitivity of a sensor described above may be estimated. The detachment of 5 micro-beads as a conservative minimum detection limit is considered. Assuming that, on average, each one is attached by 100 tethers, accumulation of 500 antigen molecules is necessary to generate a measurable signal. Diffusion of antigen to the active area of the sensor can be modeled as hemispherical diffusion to a disk with a radius of about 30 μm. Under these conditions, the diffusive flux J(r) is constant and can be expressed by:

$$J(r) = \frac{4DC^*}{\pi r} \quad (5)$$

where D is diffusion constant of the antigen (D≅1×10$^{-6}$ cm²/s) and C* [mol/cm³] is its initial bulk concentration. Clearly, accumulation of a certain number of moles (N/N$_A$) of antigen diffusing, at constant rate, to the sensors active region is directly proportional to time and the initial antigen concentration:

$$N/N_A = J(r)\pi r^2 t = 4DC^* r t \quad (6)$$

where N$_A$ is the Avogadro number, t is time, and r is the radius of the sensor containing the micro-beads responding to, for example, a particular antigenic protein. In one embodiment, the sensor radius (r) may be about 30 microns, containing 100 or 200 micro-beads. Thus allowing, for example, for a 15 min incubation time, yields a detection limit of 0.08 pM. A lower detection limit could be realized by: 1) decreasing the number of micro-spheres in the individual sensor active region (This would decrease the sensor radius (r), and thus increase the antigen flux to the sensor. It would also decrease the threshold number of detached micro-beads (assumed to be 5 in the embodiment above)); 2) decreasing the number of molecular tethers attaching each micro-sphere, or 3) increasing the incubation time. Thus, a sub-fM detection limit is realistic following proper sensor optimization. Finally, it is worth pointing out that the micro-sensor detection limit is independent of the antigen-antibody binding constant. In the calculation above, it was only assumed that the antigen modification can result in a hundred fold decrease of its natural binding constant.

Several known chemical reactions may be used to modify specific amino acid residues as a means of altering the topography of the epitope of PSA involved in binding with a specific anti-PSA IgG. (PSA is prostate specific antigen—our test case, anti-PSA is one of the PSA antibody proteins.) One of several hydrophilic amino acid residues could be randomly targeted assuming that some of them are present in the epitope region of the protein. (Epitope region is a fragment of a protein surface which is contacted by a complimentary region of its antibody to form the antigen-antibody complex.) Excessive modification, however, would destabilize antigen-antibody complex and defeat the purpose of using the modified PSA to form stable molecular tethers attaching micro-beads to the device surface.

The strength of the antibody-antigen interaction is a result of many factors, including ion pairing, hydrogen bonding, dipolar and hydrophobic interactions. See, J. Janin et al., "The structure of protein-protein recognition sites", *J. Biol. Chem.,* 1990, 265, 16027-16030, which is incorporated herein by reference. The latter include steric considerations and solvent effects. Ideally, a small modification is induced such as altering the topography of the protein surface that would, for example, decrease the extent of hydrophobic interactions or disrupt one hydrogen bond. Indeed, a loss of a single hydrogen bond would result in a decrease of the binding energy by ca 20 kJ/mol. This corresponds to changing the equilibrium constant by two orders of magnitude, as desired. On the other hand, a more significant alteration such as, for example, elimination of a salt bridge, if such exists, would likely excessively decrease the binding energy. Consequently, while little is known about the exact surface structure of the PSA epitopal region, for example, chemical modifications that eliminate charged groups are not at the top of the list of possible modifications to be explored. Bearing these general considerations in mind, the list of possible modifications includes the following:

Methylation of lysine. This can be carried out by adding mM concentrations of formaldelhyde and a reducing agent such as sodium cyanoborohydride to a protein solution in a 4-(2-hydroxyethyl)-1-piperazineethanesulfonic acid (Hepes) buffer solution. See, N. Jentoff et al., "Labeling of proteins by reductive methylation using sodium cyanoborohydride", *J. Biol. Chem.,* 1979, 254, 4359-4365, and R. H. Rice et al., "Stabilization of bovine trypsin by reductive methylation", *Biochim. Biophys. Acta,* 1977, 492, 316-321, which are incorporated herein by reference. Other reducing agents, such as sodium borohydride, have also been used, but the cyanoborohydride reaction is less harsh, and is less likely to significantly alter the overall protein structure, for example by reducing disulfide bonds. This reaction is specific to lysine and the amine terminus of the protein. It does not eliminate the positive charge on the protein surface. Finally, should the addition of a methyl group only slightly reduce the binding constant, the formaldehyde could be replaced with ethanal or propanal to add a larger ethyl or propyl group to the amine.

Methylation of histidine. This can be done using the procedure described by M. J. P. Dekker et al., "Identification of a second active site residue in *escherichia coli* I-threonine dehydrogenase: methylation of histidine-90 with methyl p-nitrobenzenesulfonate", *Arch. Biochem. Biophys,* 1995, 316, 413-420, which is incorporated herein by reference.

Briefly, a few mM of methyl p-nitrobenzenesulfonate (MNBS) is added to a protein solution in a 100 mM potassium phosphate pH 7 buffer. This results in the preferential methylation of histidine residues. Similar to the case of lysine, should a methyl group prove to insufficiently lower the binding constant, ethyl or propyl groups could be tried instead.

Modification of cysteine. This can be accomplished by following the procedure outlined by J. F. Schindler et al., "Conversion of cysteinyl residues to unnatural amino acid analogues", *J. Protein Chem.,* 1996, 15, 737-742, which is incorporated herein by reference. In this scheme, alkane chains of any length can be added to cysteine chains simply by reacting the 1-bromo or 1-iodo alkane of the desired length with the protein in a pH 9.5 buffer.

Iodination of tyrosine. In view of the size of iodine, its modification might prove excessive. The effect of this modification on the binding constant must be experimentally determined. Even if the size of iodine is excessive, tyrosine modification could prove effective if the tyrosine is located near the edge of the epitopal region. Iodination can be accomplished by adding five- to ten-fold excess of $I_2$ dissolved in KI and 25 mM sodium borate to a solution of protein. This results in the addition of 1-2 iodines per tyrosine. See, R. L. Lundblad, "Chemical Reagents for Protein Modification", 3rd Edition., CRC Press, Boca Raton, Fla. 2005 pp 213-215, which is incorporated herein by reference.

Addition of various groups to arginine. For example, when protein is added to a pH 7.4, 0.125 M Tris buffer containing 0.1 M KCl, 0.01 M $MgCl_2$ and a dilute suspension of dinitrophenol, the dinitrophenol adds to any exposed arginine residues. See, H. M. Levy et al, "Inactivation of myosin by 2,4-dinitrophenol and protection by adenosine triphosphate and other phosphate compounds", *J. Biol. Chem.,* 1963, 238, 3654-3659, which is incorporated herein by reference. Alternatively, a 3% solution of phenylglyoxal in buffer can be added to the buffered protein solution and the reaction allowed to proceed for 24 hours. This results in the addition of phenylglyoxal to arginine groups. See, K. Takahashi, "The reaction of phenylglyoxal with arginine residues in proteins", *J. Biol. Chem.,* 1968, 243, 6171-6179, which is incorporated herein by reference.

Reactions involving carboxyl groups. These schemes commonly involve Woodward's reagent K being added to the protein in an ~pH 3 solution along with a nucleophile such as ethyl amine, and results in the formation of an amide. See, R. B. Woodward et al, "A new synthesis of peptides", *J. Am. Chem. Soc.,* 1961, 83, 1010-1012, and P. Bodlaender et al, "The use of isoxazolium salt for carboxyl group modification in proteins", *Biochemistry,* 1969, 8, 4941, which are incorporated by reference herein. This scheme would eliminate a negative charge on the protein surface and might be too harsh. However, if a carboxyl group resides near the edge of the epitopal region, its modification may lead to a desired effect.

Regarding a DNA version of a sensor, it should be appreciated that the difference in the binding constants between a modified antigen and an antibody relative to native antigen-antibody complex is, in the DNA sensor 10 (FIGS. 1A-1B), intrinsically reflected in the different length of the two ssDNA fragments: one, longer bound to the sensor surface (the recognition DNA) and the other, shorter bound to a bead surface. The target DNA is expected to be longer than the ssDNA bound to the bead. As a result it will quickly be able to replace and break the tether 24.

In the case of the enzymatic cleaving of a specific peptide sequence, in another embodiment, a molecular tether would be forwarded attaching the beads to the surface using that particular peptide chain. When a sample contains the enzyme that cleaves that peptide the bead is released.

The general idea of competitive interactions between a target compound and the same compound forming a tether that attaches a micro-bead requires lability of the target compound—recognizing compound interactions. In other words, slow kinetics of ssDNA-ssDNA hybridization/dehybridization or antigen-antibody association/dissociation could require excessively long incubation times. While the kinetics of DNA hybridization has been shown to be sufficiently facile to be compatible with this sensor's principle of operation, the kinetics of antigen-antibody binding has not been investigated in many cases. The available data suggest that the range of the dissociation rate constants ($k_{off}$) exhibited by the various antigen-antibody complexes spans several orders of magnitude from about $10^3$ to $10^{-5}$ $s^{-1}$. Clearly, those antigens which exhibit $k_{off}$ values of their antigen-antibody complexes smaller than about $10^{-2}$ $s^{-1}$ could not be easily detected with the technique described above. In those cases, an alternative strategy exists. It involves the reverse of the competitive binding approach discussed above.

For example, in the embodiment of FIG. 4, the device surface would be populated with the antibodies specific for a particular target antigen, but would not contain any micro-beads. Micro-beads would also carry on their surface a small number density of the antibody molecules for the target antigen. Initially, a small volume of the analyte solution would be deposited onto the channel surface and incubated. The antigen, if present, would bind to the antibodies on the sensor surface. Next, after a rinse, a second incubation would expose the device to a suspension of micro-beads carrying on their surface monoclonal antibodies specific for a different part, epitope of the antigen, or a polyclonal antibody (a mixture of antibodies specific for the same antigen but recognizing and binding to its various fragments). This will result in attachment of the beads to the device surface. Following a rinse, as discussed above, the E vs t transient would report the population density of the beads which in turn would allow a determination to be made as to the presence and concentration of the target antigen protein in the sample. The reverse scheme, of course, could also be used for DNA and peptide sensing.

In a reverse approach, in the embodiment of FIGS. 5 and 6, the presence of specific antibody could be determined. To accomplish this, a target antibody would be first chemically modified to get Ab'. It would then be used to attach micro-beads to the sensor surface. The same attachment protocol would be used except native (unmodified) PSA antigen, for example, would now be used. Now, exposure of a sensor to a small volume of a serum sample would result in bead release if a PSA antibody is present. This is because that native, unmodified antibody would easily replace the modified antibody in the attaching tether and thus break the linkage.

A generally applicable signal transduction mechanism designed to function in a hand-held biological sensor and sensor arrays has been described. Two applications of the transduction mechanism have been presented. One application is targeting immunogens (antigens), a large group of macromolecules (for example cancer-specific proteins, toxins and numerous other pathogens) capable of inducing a humoral immune response, in other words, inducing the generation of antibodies. The antigens must be poly- or at least bivalent (exhibiting more than one epitope, an active region on the surface of an immunogenic macromolecule involved in selective binding with the antibody). Since essentially all large macromolecules exhibit this property, this class of biological sensors is designed to target a broad range of antigens. The second application deals with DNA sensing. Indeed, in both of these areas, few, if any, generally applicable signal transduction schemes exist that could be relied on in sensor design. Indirect techniques such as enzyme-linked immunosorbent assay (ELIZA) and assays relying on the polymerase chain reaction (PCR) for signal amplification are not compatible with sensor methodology as they involve secondary reagents and time consuming processes.

A sensor of the present invention uses a signal transduction mechanism that is adaptable to a range of biological or chemical sensors. It can translate a chemical event, even a singular molecule chemical event, into an electrical readout. The signal transduction mechanism also incorporates a substantial amplification factor in that a single molecule event, such as DNA hybridization, could result in the release of a microscopic object, for example, a microbead.

Additionally, other strategies exist for determining the number of beads released from the surface of the sensor channel relative to those that remain bound to the channel surface. These strategies can be grouped into two categories: (1) Those that can count the beads by measuring changes in the volume of a solution confined within a sensor channel occupied by the beads. These systems or methods require that the channel encompassing the beads be of the same dimensions before and after the chemical step resulting in bead release. (2) Those that count released beads using a direct method.

The above-discussed signal transduction mechanism illustrated in FIGS. 1A-2C is an example of the first group, that is, a system or technique involving measurements of the solution volume change in the sensor channel. Other such system and techniques include conductivity measurements, coulometric measurements and spectrometric measurements.

Conductivity measurements are often used in liquid chromatography detectors. The beads would be confined to a sensor channel of a fixed height or thickness (h) with two metal, for example, gold, electrodes constituting the opposing plates of the channel. The conductance of the solution between the plates is proportional to the concentration of an inert electrolyte, for example KCl, in the channel; the spacing between the electrodes; and the bead population density (the lower the bead density the higher the conductance of the electrolyte solution).

A technique involving coulometric measurements of a redox spectator species in a solution in the sensor channel could also be used. Such a system would require that one of the opposing plates of the sensor channel be coated with a metal, such as gold, and serve as a working electrode. If the solution in the channel contained redox active molecules of a known concentration, the total charge collected during their electrochemical reduction or oxidation can be interpreted in terms of the population density of the beads in the sensor channel. One of a number of redox active species could be selected for this purpose. For example, ferric ions ($Fe^{3+}$), oxygen ($O_2$) naturally present in water equilibrated with air, ascorbic acid (vitamin C), or chloride ions ($Cl^-$, chloride is not directly electro-active but its content could be quantified by electro-oxidation of silver) could be used.

Spectrometric measurements of the absorbance due to a spectator species in the channel could also be employed. Here, the solution in the channel of the sensor would contain species absorbing light in a particular range of wavelengths of the visible region. Numerous inexpensive, water soluble, organic dye molecules, for example, such as those used as food coloring compounds, could be used. Transparent glass or polymeric beads would be required in this case. A small light beam from a light emitting diode or a similar light source would be directed to pass through the channel in between and parallel to the plates creating the channel. Measurements of the light intensity with a small solid-state optical sensor could be then interpreted in terms of the bead population in the sensor channel.

The second group involves the direct measurement of the bead population in the sensor channel. For example, the embodiment of FIG. 6 uses an optical microscope to detect bead detachment. Other optical measurement and electrochemical bead counting techniques can be used.

One optical measurement of the bead number density in the sensor channel is similar to the spectrometric measurement technique described above, except the beads would be made light absorbing. This could be done in a number of ways such as by immobilization of light absorbing dye molecules on the bead surface or by incorporating a light absorbing compound into the bead forming material. Detection of the light passing through the sensor channel would indicate the number of the beads in the path of the light beam. This measurement would not require that the channel be of some known height.

The beads in the sensor channel could also be electrochemically counted. This system would require that the beads contain a magnetic core, for example, one made of ferric oxide, and that they be electrochemically-active. Several different strategies could be used to accomplish the latter. For example, the surface of the beads could be coated with a thin film carrying electrochemically active molecules. Alternatively, the beads could be over-coated with a thin film of a metal, such as silver. The latter could be converted electrochemically to a coating of AgCl. The sensor would comprise of two plates positioned parallel to each other at a distance larger than a bead diameter. A small permanent magnet would be positioned above the top plate. The bottom surface of the top plate would be coated with, for example, gold, and would function as a working electrode. Any released beads would be attracted to the top plate by the magnetic force and thus make electrical contact with the electrode. The latter would be held at a constant potential at which redox molecules on the bead surface or the silver coating (in presence of chloride ions) would be electrochemically oxidized or reduced, generating a certain fixed electrical charge per bead. Thus, the total charge collected would be directly proportional to the number of the beads released from the sensor surface.

Similarly, metal coated beads, for example, gold-coated beads, that do not carry any redox active molecules could also be used. Here, when the beads contact the top plate electrode, which is held a constant potential, a charge would flow due to electrical charging of the surface of the metal coated beads. This charge would be proportional to the bead surface area and would likewise indicate its release form the sensor channel surface. The total charge due to this electrochemical "double-layer charging" of the individual beads would be again proportional to the total number of the released beads.

In summary, the sensor strategy outlined above involves two chemically and physically independent processes: chemical sensing involving breaking of the molecular tethers used to attach the beads, and chemical or physical detection of the resulting (decreased) bead population. The latter can be accomplished in a number of different ways as shown above.

In view of this general two step operation mode (chemical/biological sensing, and signal transduction generating an electrical, easy to measure signal), it is apparent to recognize that this entire scheme, as also discussed above, could also be implemented in reverse order. Specifically, chemical/biological sensing could be reconfigured to result in bead attachment, starting with beads attached to the device surface. The signal transduction would then report the increase of the bead population attached to the device surface using one of the several techniques discussed above.

Although many of the components and processes are described above in the singular for convenience, it will be appreciated by one of skill in the art that multiple components and repeated processes can also be used to practice the techniques of the present invention.

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. A method to determine if a target substance is present in an analyte comprising:
providing a plurality of beads attached to a surface of a sensor by a molecular tether configured and arranged to be selectively cleaved in the presence of a target substance to release at least one of the beads from the surface of the sensor wherein the target substance is a single-stranded DNA target and a molecular tether is a hybridized double-stranded DNA tether with one of the single-stranded DNA fragments of the double-stranded DNA tether being complementary to the DNA target;
using a magnet positioned above the surface of the sensor to apply a force on the beads in a direction opposite that of a tether and to remove from the surface of the sensor at least one of the beads as a result of the molecular tether being cleaved in a course of a reaction with the target substance while in the field of the force applied by the magnet; and
determining by use of a measurement system the population of beads attached to the sensor surface after the introduction of the analyte.

2. The method of claim 1, wherein the hybridized double-stranded DNA tether includes first and second single-strand DNA fragments, the first single-strand DNA fragment being attached to a surface of the sensor, the sequence of the first single-strand DNA fragment being complementary to the DNA target, and the second single-strand DNA fragment being attached to a surface of a bead.

3. The method of claim 1, wherein the measurement system is a signal transduction system, a conductivity measurement system, a coulometric measurement system, a spectrometric measurement system, an optical measurement system, or an electrochemical counting system.

4. A method to detect a target substance in an analyte comprising:
providing a plurality of beads attached to a surface of a sensor by molecular tethers configured and arranged to be selectively cleaved in the presence of a target substance to release at least one of the beads from the surface of the sensor;
applying an external magnetic force perpendicular to the surface of the sensor to act on the beads in a direction opposite that of a tether and to remove from the surface of the sensor at least one of the beads as a result of a molecular tether being enzymatically cleaved in a course of a reaction with the target substance while in the field of the applied magnetic force; and
determining the population of beads in the sensor after the introduction of the analyte into the sensor.

5. A method to determine if a target DNA is present in an analyte comprising: providing a plurality of beads attached to a sensor surface, prior to an initial introduction of the analyte into a sensor, by hybridized double-stranded DNA tethers, with one of the single-stranded DNA fragments of the double-stranded DNA tethers being complementary to the target DNA such that as a result of a competitive exchange interaction with the target DNA at least one tether is broken and at least one of the beads is released from a sensor surface in the presence of the target DNA, wherein each tether has a proximal end and a distal end, and is attached to the sensor surface at the proximal end and is attached to the bead at the distal end, and using a magnet positioned above the sensor surface to apply a force on the beads in a direction opposite that of the tethers and to remove from the sensor surface at least one of the beads as a result of a tether being cleaved in a course of a reaction with the target DNA while in the field of the force applied by the magnet.

6. The method of claim 5, wherein at least one of the plurality of beads is attached to the sensor surface by a plurality of tethers.

7. The method of claim 5, wherein as a result of competitive exchange interaction a duplex between the target DNA and a strand of the tether is formed.

8. The method of claim 5, wherein the sensor comprises a channel defined by a top plate and a bottom plate, wherein the sensor surface is an interior surface of the bottom plate.

9. The method of claim 5, wherein the distance between the top and bottom plates is based on a bead diameter.

10. The method of claim 5, wherein the sensor further comprises first and second electrodes, wherein the plurality of beads tethered to the sensor surface are disposed between the first and second electrodes.

11. A method to determine if a target antigen is present in a sample comprising: providing a plurality of beads attached to a surface of a sensor, prior to an initial introduction of the sample into the sensor, by molecular tethers which include a modified antibody-antigen complex with the modified antibody-antigen complex having a lower binding constant than the target antigen such that as a result of a competitive exchange interaction with the target antigen at least one tether is broken and at least one of the beads is released from the surface of the sensor in the presence of the target antigen, and using a magnet positioned above the surface of the sensor to apply a force on the beads in a direction opposite that of the tethers and to remove from the surface of the sensor at least one of the beads as a result of a tether being cleaved in a course of a reaction with the target antigen while in the field of the force applied by the magnet.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Selected as an example of a study designed to
      test the behavior of the sensor.

<400> SEQUENCE: 1
tgtgctagta cagac                                                      15

<210> SEQ ID NO 2
<211> LENGTH: 24
<212> TYPE: DNA
<213> ORGANISM: Artificial Sequence
<220> FEATURE:
```

```
<223> OTHER INFORMATION: Selected as an example of a study designed to
      test the behavior of the sensor.

<400> SEQUENCE: 2
agatcagtgc gtctgtacta gcac                                              24
```